United States Patent
Weisse et al.

[11] Patent Number: 5,360,936
[45] Date of Patent: Nov. 1, 1994

[54] PROCESS FOR THE PREPARATION OF SUBSTITUTED INDANONES

[75] Inventors: Laurent Weisse, Oberursel; Heinz Strutz, Usingen, both of Germany

[73] Assignee: Hoechst Aktiengesellschaft, Frankfurt, Germany

[21] Appl. No.: 120,104

[22] Filed: Sep. 10, 1993

[30] Foreign Application Priority Data

Sep. 11, 1992 [DE] Germany ............... 4230373

[51] Int. Cl.$^5$ ............... C07C 45/45
[52] U.S. Cl. ............... 568/319; 568/323; 568/322
[58] Field of Search ............... 568/319, 323, 322

[56] References Cited

U.S. PATENT DOCUMENTS

2,456,452  12/1948  Seeger ............... 260/590

FOREIGN PATENT DOCUMENTS

| 1249302 | 1/1989 | Canada | C07C 49/784 |
| 2094980 | 10/1993 | Canada | C07C 49/665 |
| 162465 | 11/1985 | European Pat. Off. | C07C 49/67 |
| 0202403 | 11/1986 | European Pat. Off. | 568/319 |
| 631003 | 12/1927 | France . | |
| 51-65742 | 6/1976 | Japan | 568/319 |
| 60-188343 | 9/1985 | Japan | 568/323 |

OTHER PUBLICATIONS

Fieser et al., "Inter- and Intramolecular Acylations with Hydrogen Fluoride," *J. Am. Chem. Soc.* (1939), vol. 61, pp. 1272–1281.

Hart et al., "Acylation–Alkylation Studies. I," *J. Am. Chem. Soc.* (1950), vol. 72, pp. 3286–3287.

*Primary Examiner*—James H. Reamer
*Attorney, Agent, or Firm*—John M. Genova

[57] ABSTRACT

1-Indanones of the formula IV or IVa

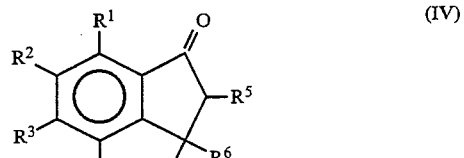

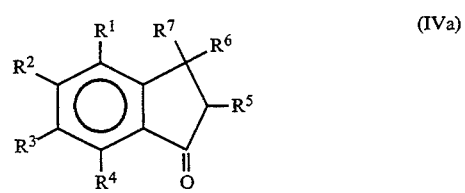

in which $R^1$ to $R^7$ are preferably hydrogen or alkyl, or adjacent radicals $R^1$ to $R^4$ form a ring, are obtained in a one-step reaction by reacting a compound I

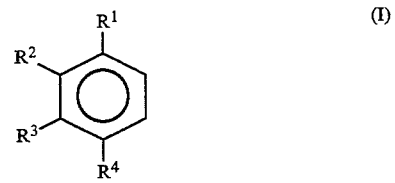

with a compound of the formula II

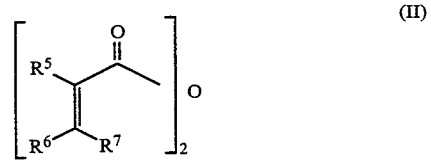

or with a compound of the formula (III)

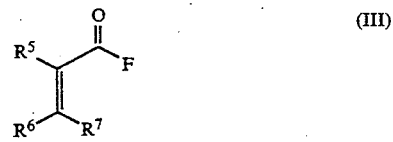

in anhydrous hydrogen fluoride and with boron trifluoride.

6 Claims, No Drawings

PROCESS FOR THE PREPARATION OF SUBSTITUTED INDANONES

DESCRIPTION

The present invention relates to a technically simple process for the preparation of substituted 1-indanones.

Compounds of this type are important intermediates in the preparation of metallocene complexes, since 1-indanones can readily be converted into the corresponding indenes. Indenes are used as a ligand system for the synthesis of metallocene complexes (EP-A 336 128).

Furthermore, substituted 1-indanones are of industrial importance as scents (EP-A 162 465) and as valuable intermediates in the preparation of pharmaceutical products or other bioactive compounds (EP-A 421 759; J. Med. Chem. 25 (1990) 765).

A number of processes for the preparation of substituted 1-indanones are described in the literature.

1-Indanones which carry substituents on the six-membered ring can be prepared starting from the correspondingly substituted aromatic compounds by fusing the five-membered ring on in 2- to 6-step syntheses (J. Org. Chem., 55 (1990) 247; Bull. Soc. Chim. Fr. 6 (1969) 1981).

Processes for the preparation of 1-indanones which carry substituents on the five-membered ring or on both rings are likewise known (J. Org. Chem. 46 (1981) 3758; J. Org, Chem. 23 (1958) 1441).

These methods have the disadvantage that they are generally multistep and give only poor overall yields of the desired products. Many of the syntheses cannot be applied generally, but are restricted to specific derivatives. In others, the starting materials are again not readily available or are very expensive. Certain substitution patterns on the aromatic ring are likewise impossible to achieve by these methods. The few known one-step syntheses have the disadvantage that they are restricted to specific derivatives and give poor yields, so that technically complex purification operations of the products are necessary. Most of these reactions are carried out with the aid of Friedel-Crafts catalysts, such as, for example, ALCl3, which are employed in excess. These reactions require technically complex work-up steps, which are associated with production of a large amount of salt.

Also known are processes for the preparation of substituted indanones by reacting aromatic compounds, such as xylene or acenaphthene, with aqueous methacrylic acid, crotonic acid or cinnamic acid in a large excess of liquid hydrogen fluoride (J. Am. Chem. Soc. 61 (1939) 1272; J. Am. Chem. Soc. 72 (1950) 3287). The yields are between 62% and 81%. This method has the disadvantage that water which is present or formed significantly reduces the activity of the Friedel-Crafts catalyst. This results in low yields and corrosion problems.

EP 93 106 649.2 describes a process which enables the preparation of substituted 1-indanones in one step from relatively inexpensive starting compounds. In the case of certain starting materials, this method gives two or more isomers, it being virtually impossible to preferentially prepare one of these isomers. In the case of highly deactivated aromatic compounds, this process is in addition very time consuming or unsuitable.

The object was therefore to find a process for the preparation of the abovementioned indanones which avoids the disadvantages known from the prior art.

Surprisingly, it has been found that aromatic compounds of the formula I below react with commercial carboxylic anhydrides of the formula II or carboxylic acid fluorides of the formula III in liquid hydrogen fluoride and with boron trifluoride rapidly, virtually quantitatively and even under relatively mild conditions to give indanones of the formula IV/IVa. In addition, certain indanones which, according to the prior art, were only accessible by complex syntheses can be prepared in one step.

The present invention therefore relates to a process for the preparation of a compound of the formula IV or the isomer thereof of the formula IVa

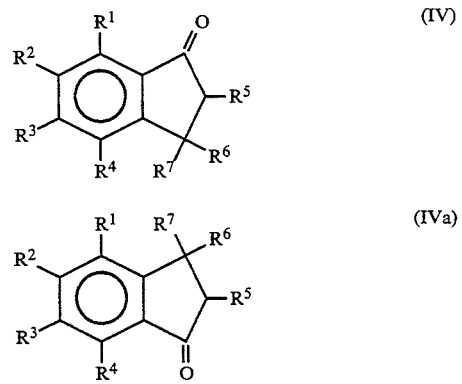

in which
$R^1$, $R^2$, $R^3$, $R^4$, $R^5$, $R^6$ and $R^7$ are identical or different and are hydrogen, $(C_1-C_{20})$alkyl, $(C_6-C_{14})$aryl, $(C_1-C_{10})$alkoxy, $(C_2-C_{10})$alkenyl, $(C_7-C_{20})$arylalkyl, $(C_7-C_{20})$alkylaryl, $(C_6-C_{10})$aryloxy, $(C_1-C_{10})$fluoroalkyl, $(C_6-C_{10})$haloaryl, $(C_2-C_{10})$alkynyl, an $-SiR^8_3$ radical where $R^8$ is $(C_1-C_{10})$alkyl, or are a halogen atom or a heteroaromatic radical having 5 or 6 ring members which may contain one or more heteroatoms, or adjacent radicals $R^1$-$R^4$, together with the atoms connecting them, form one or more substituted or unsubstituted rings, which comprises reacting a compound of the formula I

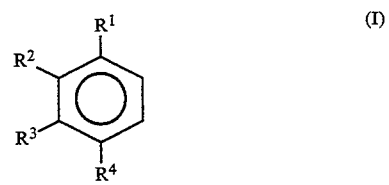

with a compound of the formula II

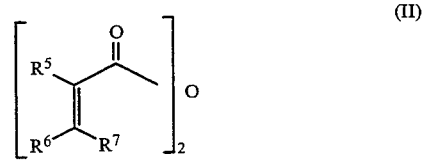

or with a compound of the formula (III)

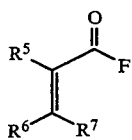

in which $R^1$-$R^7$ are as defined above, in liquid, anhydrous hydrogen fluoride and with boron trifluoride.

In these formulae, alkyl is straight-chain or branched alkyl. Halogen is fluorine, chlorine, bromine or iodine, in particular fluorine or chlorine. Examples of heteroaromatic radicals are thienyl, furyl and pyridyl.

In the formulae IV and IVa, it is preferred that $R^1$, $R^2$, $R^3$ and $R^4$ are identical or different and are hydrogen, $(C_1-C_{10})$-alkyl, $(C_1-C_4)$-alkoxy, $(C_2-C_6)$-alkenyl, $(C_6-C_{14})$-aryl, $(C_1-C_6)$-fluoroalkyl, $(C_6-C_{14})$-aryloxy or a halogen atom, or the radicals $R^1$ and $R^2$, $R^2$ and $R^3$ or $R^3$ and $R^4$, together with the atoms connecting them, form a five- or six-membered ring, and $R^5$, $R^6$ and $R^7$ are identical or different and are hydrogen, $(C_1-C_{10})$-alkyl or $(C_6-C_{14})$-aryl.

The rings formed by adjacent radicals $R^1$-$R^4$ can be substituted by substituents as defined for $R^1$-$R^7$, or the preferred meanings mentioned therefor.

It is particularly preferred that $R^1$, $R^2$, $R^3$ and $R^4$ are identical or different and are hydrogen, $(C_1-C_{10})$-alkyl, $(C_6-C_{14})$-aryl, $(C_2-C_4)$-alkoxy or a halogen atom, or the radicals $R^1$ and $R^2$, $R^2$ and $R^3$ or $R^3$ and $R^4$, together with the atoms connecting them, form a five- or six-membered, preferably six-membered, saturated or unsaturated carbocyclic ring, and $R^5$, $R^6$ and $R^7$ are identical or different and are hydrogen, methyl or phenyl.

The saturated or unsaturated five- or six-membered (carbocyclic) ring formed by adjacent substituents $R^1$-$R^4$ may additionally carry substituents, preferably $(C_1-C_{10})$alkyl.

Examples which may be mentioned of compounds of the formulae IV and IVa are:
6,7-benzo-2-methylindan-1-one,
4,5-benzo-2-methylindan-1-one,
5,7-diisopropyl-2-methylindan-1-one,
4,6-diisopropyl-2-methylindan-1-one,
2,5-dimethylindan-1-one,
2,6-dimethylindan-1-one,
5-isobutyl-2-methylindan-1-one,
2,5,7-trimethyl-1-indanone,
2,4,6-trimethyl-1-indanone,
2-methylindan-1-one,
2,4,5,6-tetramethylindan-1-one,
5-phenyl-2-methylindan-1-one,
8-methyl-4,5,7,8-tetrahydrocyclopenta[e]acenaphthylen-9-one,
2-methyl-3,9-dihydro-2H-cyclopenta[b]fluoren-1-one,
2-methyl-2,10-dihydro-1H-cyclopenta[a]fluoren-3-one,
16-methyl-6,7,15,16-tetrahydrocyclopenta[a]phenanthren-17-one,
9-methyl-5,6,9,10-tetrahydro-cyclopenta[b]phenanthren-8-one,
5-methoxy-2-methylindan-1-one and
5, 6-dimethoxy-2-methylindan-2-one.

Depending on the substitution pattern on the aromatic ring, the indanones may be produced in the form of two constitutional isomers of the formulae IV and IVa. Depending on the intended application, these can be further reacted in pure form or as a mixture. In the preparation of metallocene complexes and when the 1-indanones are used as scents, the isomer mixture can be employed.

The indanones IV/IVa are preferably prepared by reacting aromatic compounds of the formula I with anhydrides of the formula II.

The starting compounds of the formula I are commercially available or can be prepared by methods known from the literature.

The carboxylic acid fluorides of the formula III can be prepared from the known carboxylic acid chlorides or carboxylic anhydrides (formula II) in a manner known from the literature by reaction with HF (cf., for example, Advanced Organic Chemistry, 1983, 399).

In the preparation of the compounds IV/IVa, additional solvent can be added to the hydrogen fluoride, but the reaction is preferably carried out in pure, anhydrous hydrogen fluoride.

The molar ratio between the compound of the formula I, the compound II or III and the hydrogen fluoride can vary within broad limits. The I:II or III:HF molar ratio is preferably from 1:0.5–2.0:5–100, in particular from 1:0.9–1.2:20–50. This means that the hydrogen fluoride is employed in excess.

If x is the total number of ether, keto, thio or carboxyl groups in the starting compounds, the molar ratio between boron trifluoride and the compound of the formula I is from (0.5–1.5) x:1.

The reaction temperature is preferably from $-30°$ C. to $130°$ C., in particular from $-10°$ C. to $80°$ C.

The reaction times generally vary between 10 minutes and 24 hours, preferably between 30 minutes and 8 hours.

Reaction is preferably carried out in the pressure range from 1 to 15 atm.

It is preferred to initially introduce a mixture of the compounds I and II (or I and III) and to meter in the hydrogen fluoride. The reverse sequence of addition is also possible.

When the reaction is complete, the hydrogen fluoride can be removed by distillation and recovered virtually quantitatively without significant impurities. Recovery of boron trifluoride is also possible in principle.

The indanones of the formulae IV and IVa can be freed from acid components by washing with $Na_2CO_3$, $NaHCO_3$ or KOH solution and water and dried using conventional desiccants, such as $Na_2SO_4$, $MgSO_4$ or molecular sieves. Since the reactions are generally virtually quantitative, further purification can in most cases be omitted. However, filtration through silica gel, aluminum oxide or filtration aids, such as, for example, Celite, is frequently advisable. If necessary, further purification can be carried out by distillation, column chromatography or crystallization. If necessary, the constitutional isomers III and IIIa can be separated from one another by column chromatography on silica gel or aluminum oxide.

The process according to the invention is particularly distinguished by the fact that differently substituted 1-indanones can be obtained in a simple and short synthesis (one-step process) and in virtually quantitative yield. The space-time yields can be considerably improved compared with the prior art by the use of boron trifluoride. A further advantage of this method is the ability to optimize the product selectivity by slightly modifying the reaction conditions (for example temperature). A particular advantage is that the process according to the invention also allows the conversion of electron-deficient aromatic compounds, such as, for example, fluorobenzene, into the corresponding indanone, which was not possible by means of the previous prior art.

The indanones IV/IVa are preferably used for the preparation of metallocenes (cf., for example, EP-A 336 128) or as scents (EP-A 162 465).

The examples below serve to illustrate the invention in greater detail.

EXAMPLE A 6,7-Benzo-2-Methylindan-1-One (1) and
4,5-Benzo-2-Methyl-Indan-1-One (1a)

14 g of boron trifluoride were added to 12.6 g (98 mmol) of naphthalene, 15.8 g (103 mmol) of methacrylic anhydride and 100 g (5 mol) of hydrogen fluoride in a 250 ml stainless-steel autoclave, and were reacted at −10° C. for 1 hour. The reaction mixture was subsequently poured onto 1 kilo of ice, and the solution was neutralized by means of dilute KOH. After the aqueous phase had been repeatedly washed with ethyl acetate, the organic phases were separated off, dried and freed from solvent in vacuo, giving 18.7 g (95% yield) of a mixture of (1) and (1a) with a selectivity of 81 and 19% respectively.

COMPARATIVE EXAMPLE TO A 12.6 g (98 mmol) of naphthalene and 15.8 g (103 mmol) of methacrylic anhydride were reacted at 50° C. for 18 hours in 100 g (5 mol) of HF. Work-up was carried out analogously to Example A, giving 19 g (97% yield) of product. The selectivity was 58% of compound (1) and 39% of compound (1a).

EXAMPLE B

5-Fluoro-2-Methyl-Indan-1-One (2) 14 g (206 mmol) of boron trifluoride were added analogously to Example A to 9.6 g (100 mmol) of fluorobenzene, 15.8 g (103 mmol) of methacrylic anhydride and 100 g (5 mol) of HF, and the mixture was stirred at 50° C. for 3 hours. Work-up was carried out analogously to Example A, giving 16 g (97% yield) of a virtually colorless liquid. The selectivity to (2) was 82%.

COMPARATIVE EXAMPLE TO B 9.6 g (100 mmol) of fluorobenzene, 16 g (104 mmol) of methacrylic anhydride and 100 g (5 mol) of HF were reacted at 70° C. for 18 hours. Work-up was carried out analogously to Example A, but no 5-fluoro-2-methylindan-1-one was isolated.

EXAMPLE C

2-Methyl-5-Phenylindan-1-One (3)

15.4 g (100 mmol) of biphenyl, 16 g (104 mmol) of methacrylic anhydride, 100 g (5 mol) of HF and 14 g (206 mmol) of BF$_3$ were reacted at 50° C. for 2 hours analogously to Example A and worked up. 22 g (99% yield) of product were isolated. The selectivity to (3) was 94%.

COMPARATIVE EXAMPLE TO C 15.4 g (100 mmol) of biphenyl and 16 g (104 mmol) of methacrylic anhydride were reacted with 100 g (5 mol) of HF at 70° C. for 60 hours. Work-up carried out analogously to A gave 22.2 g (100% yield) of product. The purity was 92%.

What is claimed is:

1. A process for the preparation of a compound of the formula IV or the isomer thereof of the formula IVa

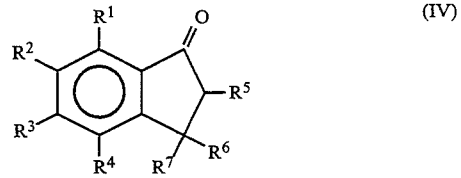

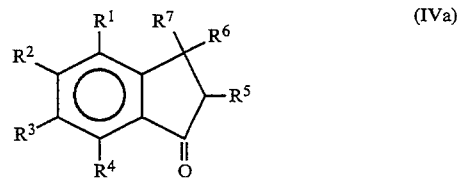

in which
R$^1$, R$^2$, R$^3$, R$^4$, R$^5$, R$^6$ and R$^7$ are identical or different and are hydrogen, (C$_1$-C$_{20}$)-alkyl, (C$_6$-C$_{14}$)aryl, (C$_1$-C$_{10}$)alkoxy, (C$_2$-C$_{10}$)alkenyl, (C$_7$-C$_{20}$)arylalkyl, (C$_7$-C$_{20}$) alkylaryl, (C$_6$-C$_{10}$)aryloxy, (C$_1$-C$_{10}$) fluoroalkyl (C$_6$-C$_{10}$) haloaryl, (C$_2$-C$_{10}$)alkynyl, an −SIR$^8$$_3$ radical where R$^8$ is (C$_1$-C$_{10}$)alkyl, or are a halogen atom or a heteroaromatic radical having 5 or 6 ring members which may contain one or more heteroatoms, or adjacent radicals R$^1$-R$^4$, together with the atoms connecting them, form one or more substituted or unsubstituted rings, which comprises reacting a compound of the formula I

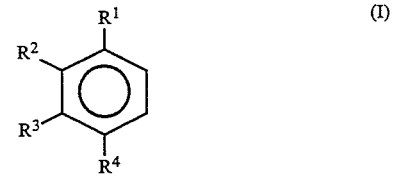

with a compound of the formula II

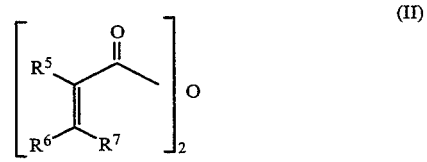

or with a compound of the formula (III)

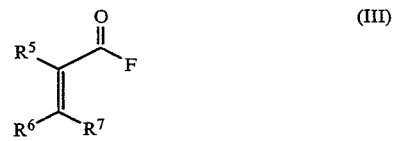

in which R$^1$-R$^7$ are as defined above, in liquid, anhydrous hydrogen fluoride and with boron trifluoride.

2. The process as claimed in claim 1, wherein, in the formulae IV and IVa, R$^1$, R$^2$, R$^3$ and R$^4$ are identical or different and are hydrogen, (C$_1$-C$_{10}$)alkyl, (C$_1$-C$_4$)alkoxy, (C$_2$-C$_6$)alkenyl, (C$_6$-C$_{14}$)aryl, (C$_1$-C$_6$)fluoroalkyl, (C$_6$-C$_{14}$)aryloxy or a halogen atom, or the radicals R$^1$ and R$^2$, R$^2$ and R$^3$ or R$^3$ and R$^4$, together with the atoms connecting them, form a five- or six-membered ring, and $R^5$, $R^6$ and $R^7$ are identical or different and are hydrogen, $(C_1-C_{10})$alkyl or $(C_6-C_{14})$aryl.

3. The process as claimed in claim 1, wherein, in the formulae IV and IVa, $R^1$, $R^2$, $R^3$ and $R^4$ are identical or different and are hydrogen, $(C_1-C_{10})$alkyl, $(C_6-C_{14})$aryl, $(C_1-C_4)$alkoxy or a halogen atom, or the radicals $R^1$ and $R^2$, $R^2$ and $R^3$ or $R^3$ and $R^4$, together with the atoms connecting them, form a six-membered, saturated or unsaturated carbocyclic ring, and $R^5$, $R^6$ and $R^7$ are identical or different and are hydrogen, methyl or phenyl.

4. The process as claimed in claim 1, wherein compound I, compound II or compound III and hydrogen fluoride have a molar ratio from 1:0.5–2.0:5–100.

5. The process as claimed in claim 1, wherein boron trifluoride and compound I have a molar ratio from $(0.5-1.5)x:1$, in which x is the total number of ether or keto groups of compound I and compound II or compound III.

6. The process as claimed in claim 1, wherein compounds of the formula IV or IVa are preferred by reacting aromatic compounds of the formula I with anhydrides of the formula II.

* * * * *